United States Patent
Tiwald et al.

(10) Patent No.: US 7,349,092 B1
(45) Date of Patent: Mar. 25, 2008

(54) SYSTEM FOR REDUCING STRESS INDUCED EFFECTS DURING DETERMINATION OF FLUID OPTICAL CONSTANTS

(75) Inventors: Thomas E. Tiwald, Lincoln, NE (US);
John A. Woollam, Lincoln, NE (US);
Galen L. Pfeiffer, Lincoln, NE (US);
Blaine D. Johs, Lincoln, NE (US);
Craig M. Herzinger, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 284 days.

(21) Appl. No.: 11/256,611

(22) Filed: Oct. 24, 2005

Related U.S. Application Data (63) Continuation-in-part of application No. 11/098,669, filed on Apr. 2, 2005, now Pat. No. 7,239,391, and a continuation-in-part of application No. 10/238,241, filed on Sep. 10, 2002, now Pat. No. 6,937,341, and a continuation-in-part of application No. 09/756,515, filed on Jan. 9, 2001, now Pat. No. 6,455,853.

(60) Provisional application No. 60/183,977, filed on Feb. 22, 2000, provisional application No. 60/318,518, filed on Sep. 10, 2001, provisional application No. 60/623,633, filed on Nov. 1, 2004.

(51) Int. Cl.
*G01N 21/41* (2006.01)
*G01J 4/00* (2006.01)

(52) U.S. Cl. ........................................ 356/369; 356/135

(58) Field of Classification Search ................ 356/128, 356/135, 369
See application file for complete search history.

(56) References Cited

U.S. PATENT DOCUMENTS

| | | | |
|---|---|---|---|
| 4,076,420 A | 2/1978 | De Maeyer et al. .......... 356/73 |
| 4,159,874 A | 7/1979 | Dearth et al. ................. 356/73 |
| 4,472,633 A | 9/1984 | Motooka ................. 250/338.1 |
| 4,807,994 A | 2/1989 | Felch et al. .................. 356/326 |
| 5,313,264 A | 5/1994 | Ivarsson et al. .............. 356/73 |
| 5,329,357 A | 7/1994 | Bernoux et al. ............ 356/369 |
| 5,373,359 A | 12/1994 | Woollam et al. ............ 356/328 |
| 5,504,582 A | 4/1996 | Johs et al. .................. 356/369 |
| 5,521,706 A | 5/1996 | Green et al. ................ 356/369 |
| 5,582,646 A | 12/1996 | Woollam et al. ............ 118/708 |
| 5,625,455 A | 4/1997 | Nash et al. ................. 356/369 |
| 5,666,201 A | 9/1997 | Johs et al. .................. 356/369 |
| 5,706,212 A | 1/1998 | Thompson et al. ......... 364/525 |
| 5,757,494 A | 5/1998 | Green et al. ................ 356/369 |
| 5,872,630 A | 2/1999 | Johs et al. .................. 356/369 |
| 5,900,633 A | 5/1999 | Solomon et al. ....... 250/339.08 |
| 5,926,284 A * | 7/1999 | Naya et al. ................. 356/445 |
| 5,991,048 A | 11/1999 | Karlson et al. ............. 356/445 |
| 6,034,777 A | 3/2000 | Johs et al. .................. 356/369 |
| 6,049,220 A | 4/2000 | Borden et al. .............. 324/765 |
| 6,200,814 B1 | 3/2001 | Malmqvist et al. ........... 436/52 |
| 6,316,274 B1 | 11/2001 | Herron et al. .............. 436/518 |
| 6,738,139 B1 | 5/2004 | Synowicki et al. ......... 356/369 |
| 2002/0024668 A1 | 2/2002 | Stehle et al. |

\* cited by examiner

*Primary Examiner*—Roy M Punnoose
(74) *Attorney, Agent, or Firm*—James D. Welch (57) ABSTRACT

A system for determination of optical constants of liquids, including provision for reducing stress induced effects while obtaining data.

18 Claims, 2 Drawing Sheets

SYSTEM FOR REDUCING STRESS INDUCED EFFECTS DURING DETERMINATION OF FLUID OPTICAL CONSTANTS

CROSS-REFERENCE TO RELATED APPLICATIONS

This application is a Continuation-In-Part of application Ser. No. 11/098,669 Filed Apr. 2, 2005 now U.S. Pat. No. 7,239,391; and therevia of Allowed application Ser. No. 10/238,241 Filed Sep. 10, 2002, (now U.S. Pat. No. 6,937, 341); and therevia of application Ser. No. 09/756,515 Filed Jan. 9, 2001, (now U.S. Pat. No. 6,455,853) and therevia Claims benefit of Provisional Application Ser. No. 60/183, 977 Filed Feb. 22, 2000. This application further Claims Benefit of Provisional Application Ser. No. 60/318,518, Filed Sep. 10, 2001 via application Ser. No. 10/238,241. This application directly Claims benefit of Provisional Application Ser. No. 60/623,633, Filed Nov. 1, 2004.

TECHNICAL FIELD

The disclosed invention relates to systems for use in investigating optical properties of materials, and more particularly to a system for reducing stress induced effects during determination of optical constants of liquids which is well suited for use in polarimeter, ellipsometer and the like systems with wavelengths in VUV, UV, Visible, Infrared, Far Infrared, and Radio ranges.

BACKGROUND

As disclosed in Co-pending Allowed application Ser. No. 10/238,241, the characterization of fluid samples, such as biological samples, is increasing in importance. Further, it is known to investigate a sample placed on a first surface of a sample stage element, which sample stage element presents with first and second, typically, but not necessarily substantially parallel surfaces, by utilizing an electromagnetic beam applied from said first surface side of said sample stage element such that said beam reflects from said sample into a detector. It is further known to independently investigate a sample placed on a sample stage element first surface utilizing an electromagnetic beam applied from a second, oppositely facing surface side of said sample stage element such that said beam reflects from the sample into a detector. Of course the sample stage element must be transparent to said electromagnetic radiation applied from the second surface side thereof in order to access the sample. Further, it is to be understood that electromagnetic radiation can be of any functional wavelength, either monochromatic, (ie. laser source), or spectroscopic.

The primary motivation for the disclosed invention is found in a need to do more definitive assays and analysis in areas such as:
  antibody/antigen interactions;
  microbiology (eg. viruses, toxins etc.);
  physiological (eg. hormones);
  drugs (therapeutic and illegal).

In addition, the present invention finds application in fundamental science where, for instance, bonding mechanisms and attachment rates for proteins and/or DNA to surfaces and other biomaterials are of interest, as well as the dielectric functions of bulk fluids.

The application of Spectroscopic Ellipsometry (SE) to biologics provides utility because reflectance from Bio-films on opaque substrates is difficult to detect where intensity changes are small. In addition Surface Plasmon Resonance (SPR), while sensitive, has a limited spectral range and can be applied only to limited types of substrate materials and layer thicknesses.

It is noted that a suitable system for investigating biologics must be relatively immune to such as temperature sensitive birefringence of electromagnetic wavelength windows, which requires careful design and mounting. And, while not related to measurement apparatus, temperature sensitivity of reagents and reactions and reagent concentration sensitivity can enter artifacts into results, hence a suitable system for investigating biologics must provide means to minimize random effects therein. A robust system and method therefore should provide compensation capability, at least to compensate the identified birefringence, during data in analysis.

Another source of birefringence is pressure applied to a system to hold elements in place with respect to one another.

Continuing, while the herein disclosed invention can be used in any material system investigation system such as Polarimeter, Reflectometer, Spectrophotometer and the like Systems, an important application is with Ellipsometer Systems, whether monochromatic or spectroscopic. It should therefore be understood that Ellipsometry involves acquisition of sample system characterizing data at single or multiple Wavelengths, and/or at one or more Angle(s)-of-Incidence (AOI) of a Beam of Electromagnetic Radiation to a surface of the sample system. Ellipsometry is generally well described in a great many publication, one such publication being a review paper by Collins, titled "Automatic Rotating Element Ellipsometers: Calibration, Operation and Real-Time Applications", Rev. Sci. Instrum., 61(8) (1990).

A typical goal in ellipsometry is to obtain, for each wavelength in, and angle of incidence of said beam of electromagnetic radiation caused to interact with a sample system, sample system characterizing PSI and DELTA values, where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system. This is expressed by:

$$TAN(\psi)e^{i(\Delta)}=r_s/r_p.$$

(Note the availability of the phase DELTA (Δ) data is a distinguishing factor between ellipsometry and reflectometry).

Continuing, Ellipsometer Systems generally include a source of a beam of electromagnetic radiation, a Polarizer, which serves to impose a state of polarization on a beam of electromagnetic radiation, a Stage for supporting a sample system, and an Analyzer which serves to select a polarization state in a beam of electromagnetic radiation after it has interacted with a material system, and passed it to a Detector System for analysis therein. As well, one or more Compensator(s) can be present and serve to affect a phase angle between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because, it is noted, Rotating Compensator Ellipsometer Systems do not demonstrate "Dead-Spots" where obtaining data is difficult. They can read PSI and DELTA of a Material System over a full Range of Degrees with the only limitation being that if PSI becomes essentially zero (0.0), DELTA can not then be determined as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have "Dead Spots" at PSI near 45 Degrees). The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

Further, it is to be understood that causing a polarized beam of electromagnetic radiation to interact with a sample system generally causes change in the ratio of the intensities of orthogonal components thereof and/or the phase angle between said orthogonal components. The same is generally true for interaction between any system component and a polarized beam of electromagnetic radiation. In recognition of the need to isolate the effects of an investigated sample system from those caused by interaction between a beam of electromagnetic radiation and system components other than said sample system, (to enable accurate characterization of a sample system per se.), this Specification incorporates by reference the regression procedure of U.S. Pat. No. 5,872,630 to Johs et al. in that it describes simultaneous evaluation of sample characterizing parameters such as PSI and DELTA, as well system characterizing parameters, and this Specification also incorporates by reference the Vacuum Chamber Window Correction methodology of U.S. Pat. No. 6,034,777 to Johs et al. to account for phase shifts entered between orthogonal components of a beam of electromagnetic radiation, by disclosed invention system windows and/or beam entry elements.

A Published patent application of which the Applicants are aware is US 2002/0024668 by Stehle et al. This application discloses the use of two electromagnetic beams applied orthogonally to a sample, and one electromagnetic beam applied normally thereto through effective windows which are oriented parallel to the surface of the sample.

Other patents of which the Inventor is aware include U.S. Pat. No. 5,757,494 to Green et al., in which is taught a method for extending the range of Rotating Analyzer/Polarizer ellipsometer systems to allow measurement of DELTA'S near zero (0.0) and one-hundred-eighty (180) degrees. Said patent describes the presence of a window-like variable birefringent components which is added to a Rotating Analyzer/Polarizer ellipsometer system, and the application thereof during data acquisition, to enable the identified capability.

A patent to Thompson et al. U.S. Pat. No. 5,706,212 teaches a mathematical regression based double Fourier series ellipsometer calibration procedure for application, primarily, in calibrating ellipsometers system utilized in infrared wavelength range. Birefringent window-like compensators are described as present in the system thereof, and discussion of correlation of retardations entered by sequentially adjacent elements which do not rotate with respect to one another during data acquisition is described therein.

A patent to Woollam et al, U.S. Pat. No. 5,582,646 is disclosed as it describes obtaining ellipsometric data through windows in a vacuum chamber, utilizing other than a Brewster Angle of Incidence.

Patent to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertain to Rotating Analyzer ellipsometer systems.

Patent to Bernoux et al., U.S. Pat. No. 5,329,357 is identified as it describes the use of optical fibers as input and output means in an ellipsometer system.

U.S. Pat. No. 5,991,048 To Karlson et al. describes a system for practicing Surface Plasmon Resonance in which a light pipe arrangement is present upon which can be situated a flow cell. Sample entered to the flow cell becomes situated on the upper surface of the light pipe and light entered to the light pipe interacts with it from below, then exists and enters a multi-element detector at various angles.

U.S. Pat. No. 6,316,274 B1 to Herron et al. describes a single light source system for practicing multi-analyte homogeneous flouro-immunoassays, via detecting of reflected and transmitted beams.

U.S. Pat. No. 5,313,264 to Ivarsson et al. describes a single light source system in which a light beam accesses a sample via a prism, (which can be semicircular in shape), and reflects into a detector.

U.S. Pat. No. 4,159,874 to Dearth et al. describes another single light source system which includes upper and lower sensors.

U.S. Pat. No. 6,200,814 B1 to Malmquist et al. describes a method and system for providing laminar flow over one or more discrete sensing areas.

U.S. Pat. No. 4,076,420 to De Maeyer et al. describes a system for investigating fast chemical reactions by optical detection of, for instance, absorption or fluorescence or scattered light, including detection of polarized light.

Patents identified during the preparation and prosecution of Pending application Ser. No. 09/756,515, from which this Application is a CIP are:

U.S. Pat. No. 5,625,455 to Nash et al.;

U.S. Pat. No. 5,486,701 to Norton et al.;

U.S. Pat. No. 5,900,633 to Solomon et al.;

U.S. Pat. No. 4,807,994 to Felch et al.;

U.S. Pat. No. 4,472,633 to Motooka;

U.S. Pat. No. 6,049,220 to Borden et al.

U.S. Pat. No. 6,738,139 to Synowicki is disclosed as it describes determining optical constants of fluids using thin films thereof.

Scientific Articles are also identified as follows:

"Determination of the mid-IR optical Constants of Water and Lubricants Using IR Ellipsometry Combined with ATR an Cell" Tiwald et al., Thin Solids Films, 313-314 (1998).

An article by Johs, titled "Regression Calibration Method For Rotating Element Ellipsometers", which appeared in Thin Film Solids, Vol. 234 in 1993 is also identified as it describes an approach to ellipsometer calibration.

Another paper, by Straaher et al., titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

An article by Collins titled "Automated Rotating Element Ellipsometers: Calibration, Operation, and Real-Time Applications", Rev. Sci. Instrum. 61(8), August 1990 is disclosed for the general insight to ellipsometer systems it provides.

An article by Kleim et al. titled "Systematic Errors in Rotating-Compensator Ellipsometry" published in J. Opt. Soc. Am./Vol. 11, No. 9, September 1994 is identified as it describes calibration of rotating compensator ellipsometers.

An Article by An and Collins titled "Waveform Analysis With Optical Multichannel Detectors: Applications for Rapid-Scan Spectroscopic Ellipsometer", Rev. Sci. Instrum., 62 (8), August 1991 is also identified as it discusses effects such as Detection System Error Characterization, Stray Light, Image Persistence etc., and calibration thereof.

A paper which is co-authored by an inventor herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

A paper by Nijs & Silfhout, titled "Systematic and Random Errors in Rotating-Analyzer Ellipsometry", J. Opt. Soc. Am. A., Vol. 5, No. 6, (June 1988) is also identified.

An article by Jellison Jr. titled "Data Analysis for Spectroscopic Ellipsometry", Thin Film Solids, 234, (1993) is also disclosed.

Papers of interest in the area by Azzam & Bashara;
"Unified Analysis of Ellipsometry Errors Due to Imperfect Components Cell-Window Birefringence, and Incorrect Azimuth Angles", J. of the Opt. Soc. Am., Vol 61, No. 5, (May 1971);
"Analysis of Systematic Errors in Rotating-Analyzer Ellipsometers", J. of the Opt. Soc. Am., Vol. 64, No. 11, (November 1974).

An unpublished article by Poksinski et al. titled "Total Internal Reflection Ellipsometry", describes application of total internal reflection to investigate protein using ellipsometric techniques.

Further identified is a flyer from Harrick, titled "Internal Reflection/ATR".

It is also mentioned that a book by Azzam and Bashara titled "Ellipsometry and Polarized light" North-Holland, 1977 is disclosed and incorporated herein by reference for general theory, as is a book which is authority regarding mathematical regression, (ie. a book titled Numerical Recipes in "C", 1988, Cambridge University Press.

Continuing, it is known to place a prism comprising 1st, 2nd and 3rd sides, atop of a material and direct electromagnetic radiation along a perpendicular to the 1st side thereof so that it totally internally reflects from the 2nd surface thereof, then exits via the 3rd side thereof. It is also known to place such a prism atop a liquid containing system, and apply sufficient pressure to said prism to effect good contact between said prism's 2nd side and said liquid, while applying electromagnetic radiation, as just described, to investigate optical properties of said liquid. A problem, arises, however, in that applying pressure to the prism causes it to introduce stress induced effects into obtained data.

It is also known to mount systems to be analyzed by electromagnetic radiation on vertically oriented stages such that the surface of a sample to be investigated faces laterally. When a vertical mounting is utilized, however, to monitor liquids, some means for containing liquid is necessary.

In view of the foregoing, a system was disclosed in application Ser. No. 10/238,241, Filed Sep. 10, 2002, for enabling substantially simultaneous investigation of a fluid sample with at least two electromagnetic radiation beams comprises a sample stage element having a first surface, and a second surface, typically, but not necessarily substantially parallel to said first surface. Said system further comprises a cell adjacent to said first sample stage element surface which comprises:
input and output windows;
input and output means for entering and exiting fluid sample;
an internal volume which is substantially closed but which has an opening adjacent to said sample stage element first surface such that fluid sample entered into said cell via said input means can access said adjacent sample stage surface. Said system further comprises a beam entry element in functional combination with said sample stage element second surface.

In use fluid sample is entered to said cell through said input means for entering fluid sample, and one electromagnetic radiation beam is entered through said input window of said cell which is adjacent to one surface of the sample stage element, and a second electromagnetic radiation beam is entered through said beam entry element adjacent to said sample stage element second surface. All entering and exiting electromagnetic radiation preferably enters and exits through window or beam entry element surfaces which are oriented substantially normal to the locus thereof.

It is noted that the beam entry element through which said second electromagnetic radiation beam is entered is preferably of a shape selected from the group consisting of:
prism;
half-spherical; and
half-cylinder;

and made of a material with is substantially transparent to said second beam contained wavelengths.

In addition, the cell can be separated from said sample stage first surface by gasket or "O" ring means or the like, such that fluid sample entered into said cell becomes present within said gasket or "O" ring means or the like on said sample stage first surface.

It should also be understood that at least two elements selected from the group:
sample stage element;
cell; and
beam entry element;

can be integrated into one another. For instance, the cell can be continuous with the first surface of the sample stage element, and/or the sample stage element and the beam entry element can be of a continuous construction.

An "integrated" system for enabling substantially simultaneous investigation of a fluid sample with at least two electromagnetic radiation beams can then be described as comprising a cell with effective input and output windows; input and output means for entering and exiting fluid sample and an internal volume, said integrated system further comprising a beam entry element in functional combination with said cell, and located therebelow, as the integrated system is viewed in upright side elevation. In use fluid sample is entered to said cell through said input means for entering fluid sample, and one electromagnetic radiation beam is entered through said effective input window of said cell, and a second electromagnetic radiation beam is entered through said beam entry element. As before, all entering and exiting electromagnetic radiation preferably enters and exits through effective cell window or beam entry element qjsurface(s) which are oriented substantially normal to the locus thereof. And, again, the effective input and output windows and the beam entry element, through which electromagnetic radiation beams are passed can be of a shape selected from the group consisting of:

prism;
half-spherical; and
half-cylinder.

The input and output windows can also be of separate construction. Further, in one variation the cell and beam entry element are of continuous construction.

Another recitation of a presently disclosed system for enabling substantially simultaneous investigation of a fluid sample with at least two electromagnetic radiation beams provides that said system comprise a cell, which cell comprises:

effective input and output windows;
input and output means for entering and exiting fluid sample;
an internal volume presenting with a surface therewithin.

Said system further comprises a beam entry element in functional combination with said cell, and being located, as viewed in upright side elevation, below said surface within said cell. In use fluid sample is entered to the internal volume of said cell through said input means for entering fluid sample, and one electromagnetic radiation beam is entered through said effective input window of said cell, and a second electromagnetic radiation beam is entered through said beam entry element, to the end that both said first and second electromagnetic beams interact, at the same or different magnitude oblique angles with respect to said surface in said internal volume of said cell, with said fluid sample present on said surface, and then exit and enter detector means.

Further, in any embodiment, the cell can also comprise a third window and a third electromagnetic beam can be caused to enter said internal volume therethrough at a substantially normal angle of incidence to said surface within said internal volume, transmit through, (or reflect from), said sample caused to be present on said surface, and enter a detector. Typically such a third beam will not be subject to having a polarization state imposed thereupon and is utilized to determine intensity attenuation resulting from interaction, (transmission or reflection via beam splitter), with said sample.

Note that the terminology "effective" input and output windows is present to indicate that said windows can be locations on such as a prism shaped, half-spherical shaped or half-cylinder shaped element, although a typical cell has physically separate input and output windows, and possibly a third window mounted therewithin.

Also a method of investigating fluid sample with at least two beams of electromagnetic radiation was proposed in application Ser. No. 10/238,241, that comprises the steps of:

a. providing a system as described above;
b. entering fluid sample into said cell internal volume so that it contacts said surface therewithin;
c. causing a first beam of electromagnetic radiation to, at an oblique angle, approach said sample directly, (not through said stage); and
d. causing a second beam of electromagnetic radiation to approach, at an oblique angle, said sample through said "stage" upon which it is supported.

Reflected components of each of the at least two electromagnetic beams are detected by one or more detector(s) and analyzed. (Single or multiple detector systems can be utilized). Particularly, but not exclusively, where a single detector system is used fiber optics can be used to guide electromagnetic radiation into different detector elements thereof.

It should also be appreciated that data is obtained from both "sides" of a sample present on said "stage" surface inside said cell internal volume. Use of the effective two data sets acquired as described in a simultaneous regression allows better determination of sample properties, such as uncorrelated thickness and refractive index.

Another invention method disclosed in the 241 application, of simultaneously investigating sample with at least two beams of electromagnetic radiation, comprises the steps of:

a. providing a system for enabling substantially simultaneous investigation of a fluid sample with at least two electromagnetic radiation beams, said system comprising a sample stage which has first and effective second surface sides;

such that in use one electromagnetic radiation beam is entered from the first surface side of said sample stage, and a second electromagnetic radiation beam is entered from the effective second surface side of said sample stage, each at an oblique angle thereto;

b. providing a sample on said first surface of said sample stage;

c. causing a first beam of electromagnetic radiation to approach said sample on said first surface from the first surface side of said sample stage; and d. substantially simultaneously with step c. causing a second beam of electromagnetic radiation to approach said sample on said first surface of the sample stage from the second effective surface side of said sample stage.

It is noted that the terminology "substantially simultaneously" is to be interpreted to include per se. simultaneous and at times separated by short delays, (eg. milli-seconds to seconds or longer).

It is also noted that the terminology "effective" second surface is used to indicate that said "effective" second surface need not be parallel to the first surface upon which is caused to be present sample. In particular an "effective" second surface can be a perimeter surface of a prism, half-spherical or half-cylinder shaped beam entry element which is affixed to a cell, said beam entry element forming what might be termed a base to said cell.

Further, it should be appreciated that two electromagnetic beams can be of similar or different polarization states, wavelength content, can be applied at the same or different angles-of-incidence to a sample on the internal surface of the cell, and can be substantially simultaneously applied by elements of one, or more than one, ellipsometer system(s). For instance, a source of electromagnetic radiation can be configured to provide two beams, one beam being applied from the one side, and one from the other side of a sample stage. The two beams can be, for instance, guided via optical fibers from one or more than one sources. And, reflected beams can be caused to enter different detectors or the same detector, (eg. as directed by optical fibers).

A preferred 241 application embodiment provided that an electromagnetic beam directed toward one side of a sample stage surface be comprised of wavelength content which differs from that of a second beam of electromagnetic radiation directed to enter from the other of said sample stage surface. Another preferred embodiment provides that the two electromagnetic beams have similar, or different, wavelength contents but are directed toward the sample stage surface at different oblique angles-of-incidence, (one from above and one from below the sample stage as the system is viewed in elevation). Another preferred embodiment provides that the two electromagnetic beams have similar, or different polarization states imposed thereupon.

It is specifically noted that the first and/or second electromagnetic beams mentioned above can be provided by a selection from the group consisting of:
  ellipsometer;
  polarimeter;
which monitor changes in both the ratio of magnitudes of orthogonal components of an electromagnetic beam and the phase angle therebetween, as a result of interaction with a sample; or by a selection from the group consisting of:
  reflectometer; and
  spectrophotometer;
which monitor change in intensity before and after interaction with a sample, although the later selections are not as relevant because birefringence of materials in intensity measurements is not typically a critical factor.

It is emphasized that the foregoing disclosed application of ellipsometric beams to, at oblique angles of incidence, investigate a sample from two sides thereof. It is again noted that a third electromagnetic beam, (eg. an unpolarized intensity beam), can be applied substantially normal to the effective surface upon which is present a fluid sample to enable acquiring beam attenuation transmission data, and said data can also be used in sample analysis.

U.S. Pat. No. 5,872,630 methodology for calibration of an ellipsometer, and U.S. Pat. No. 6,034,777 methodology for breaking correlation between the effects of the input and output windows and a sample being investigated, which methodology was recited in the Background Section, can of course be added to the preceding recitations to provide more complete methodology.

The beam entry element can be made of ZnSe, Ge or Si, (with specific tradename examples being KRS-5, and INTRAN), to provide Infrared transparency, with the cell windows being transparent to UV, Visible and Near Infrared.

A need exists for a system which contains a liquid in a cavity while data is obtained by applying electromagnetic radiation through a prism affixed thereto, to investigate optical properties of said liquid, wherein the system comprises a means for affixing said prism without inducing birefringence causing stress therein.

DISCLOSURE OF THE INVENTION

The disclosed invention is a system and method for reducing stress in optical elements used to receive electromagnetic radiation, direct it to a sample, and then mediate its receipt by a detector. For instance, the optical element might be pyramid shaped and applied to allow monitoring liquid adjacent to a side thereof which is caused to be in contact with the liquid. Common practice is to secure the optical element in position by applying force to an apex thereof which is opposite said side thereof in contact with said liquid. The present invention system comprises an additional element to which force can be applied instead of said apex.

An embodiment of the disclosed invention is a system for use in investigating optical properties of a liquid comprising:
  a prism element comprising first, second and third substantially flat sides, the second side of which is extended laterally beyond projected meeting points with the first and third sides;
  a second element comprising closed sides and top and an open bottom.

The laterally extended second side of said prism is placed into functional contact with said second element at the bottom thereof to form a liquid containing cavity, such that leakage of liquid which is caused to be present in said liquid containing cavity does not occur through said contact point. In use liquid is caused to be present in said liquid containing cavity and electromagnetic radiation is caused to enter said first or third side of said prism, interact with said second side thereof, and totally internally reflect through said third or first side thereof, respectively.

A modified present invention system for use in investigating optical properties of a liquid comprises:

a prism comprising first, second and third sides;

an intermediate element;

a third element comprising closed sides and top and an open bottom;

wherein said second side of said prism is affixed to said intermediate element by substantially stress free means, and wherein said intermediate element when placed into contact with the bottom of said third element forms a liquid containing cavity, said third element and intermediate element being forced into functional contact with one another such that leakage of liquid caused to be present in said liquid containing cavity does not occur through said contact point. In use liquid can be caused to be present in said liquid containing cavity and electromagnetic radiation can be caused to enter said first or third side of said prism, interact with said second side thereof, totally internally reflect and exit through said third or first side thereof.

The disclosed invention is a system and method for reducing stress in optical elements used to receive electromagnetic radiation, direct it to a sample and then mediate its receipt by a detector. For instance, the optical element might be pyramid shaped and applied to allow monitoring liquid adjacent to a side thereof, with common practice being to secure it in position by applying force to an apex thereof which is opposite said side. The present invention system comprises an additional element to which force can be applied instead of said apex. Said intermediate element can comprise a cavity sequestered within said intermediate element, and said cavity can be filled with a fluid. Alternatively, such a cavity in the intermediate element can be continuous with the liquid containing cavity of the third element. Another embodiment provides that the prism and intermediate element are of single piece construction.

A variation of the system for use in investigating optical properties of a liquid comprises:
  a half sphere or half cylinder element comprising a first curved and second substantially flat side, the second side of which is extended laterally beyond the points of intersection with the first curved side;
  a second element comprising closed sides and top and an open bottom;

the laterally extended second side of said half sphere or half cylinder being placed into functional contact with said second element at the bottom thereof to form a liquid containing cavity; such that leakage of liquid which is caused to be present in said liquid containing cavity does not occur through said contact point;

such that in use liquid is caused to be present in said liquid containing cavity and electromagnetic radiation is caused to enter said first curved side of said half sphere or half cylinder, interact with said second side thereof, and totally internally reflect through said first curved side of said half sphere or half cylinder, respectively.

Another variation of the present invention system for use in investigating optical properties of a liquid comprises:

a half sphere or half cylinder comprising first curved and second substantially flat side;

an intermediate element;

a third element comprising closed sides and top and an open bottom;

wherein said second substantially flat side of said half sphere is affixed to said intermediate element by substantially stress free means, and wherein said intermediate element when placed into contact with the bottom of said third element forms a liquid containing cavity, said third element and intermediate element being forced into functional contact with one another such that leakage of liquid caused to be present in said liquid containing cavity does not occur through said contact point;

such that in use liquid can be caused to be present in said liquid containing cavity and electromagnetic radiation can be caused to enter said first side of said half sphere or half cylinder, interact with said second substantially flat side thereof, totally internally reflect and exit through said first half sphere or half cylinder first side thereof.

It is noted that the foregoing description described the present invention system as viewed in elevation with one element thereof having an open "bottom". It is to be understood that the system can be rotated to orient the open "bottom" so that it faces other than downward and remain within the scope of the invention.

A present invention method of determining the optical properties of a liquid comprising the steps of:

a) providing a system for use in investigating optical properties of a liquid comprising a selection from the group consisting of:

a prism element comprising first, second and third substantially flat sides, the second side of which is extended laterally beyond projected meeting points with the first and third sides; and a half sphere or half cylinder element comprising a first curved and second substantially flat side, the second side of which is extended laterally beyond the points of intersection of first curved side;

said system further comprising a second element comprising closed sides and top and an open bottom;

the laterally extended second side of said prism, half sphere or half cylinder element being placed into functional contact with said second element at the bottom thereof to form a liquid containing cavity, such that leakage of liquid which is caused to be present in said liquid containing cavity does not occur through said contact point;

such that in use liquid can be caused to be present in said liquid containing cavity and electromagnetic radiation can be caused to enter said first curved side of said half sphere or half cylinder element, or enter said first or third side of said prism, interact with said second substantially flat side of said half sphere or half cylinder element or said prism, totally internally reflect therefrom and exit through said first curved side of said half sphere or half cylinder element or said third or first side thereof, respectively;

b) causing said liquid containing cavity to contain a liquid;

c) causing electromagnetic radiation to enter said first curved side of said half sphere or half cylinder element or enter said first or third side of said prism, interact with said substantially flat second side thereof, totally internally reflect and exit through said curved side of said half sphere or half cylinder element or said third or first side thereof respectively and enter a detector;

d) analyzing data provided by the detector in response to the electromagnetic radiation that enters thereinto to the end that optical properties of the liquid are determined.

Said method can involve application of a system involving an intermediate element that extends laterally beyond projected meeting points with the first and third sides, or laterally beyond the points of intersection of first curved side, to which said prism, half sphere or half cylinder element is affixed; or the prism, half sphere or half cylinder element and intermediate element can be merged into a single continuous element.

An additional step can comprise rotating the system to orient the open "bottom" so that it faces other than downward.

The present invention will be better understood by reference to the Detailed Description in conjunction with the Drawings.

DETAILED DESCRIPTION

Figure 1:
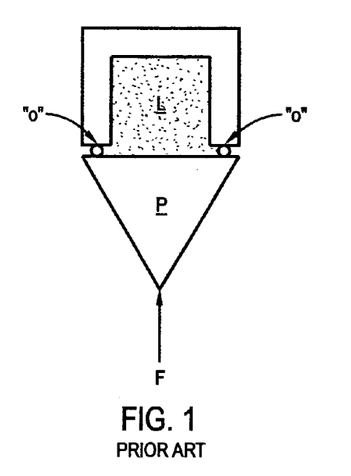
FIG. 1 shows Prior Art wherein a Liquid (L) containing Cavity is forced against a Prism (P) by applying Force (F) to said Prism.

Turning now to the Drawings, FIG. 1 shows Prior Art wherein a Liquid (L) containing Cavity is forced against a Prism (P) by applying Force (F) to said Prism. Said Force (F) can cause stress in the Prism and induce artifacts to data obtained by causing electromagnetic radiation to pass through said Prism (P), interact with the Prism (P)-Liquid (L) interface, and exit said Prism (P).

Figure 2:
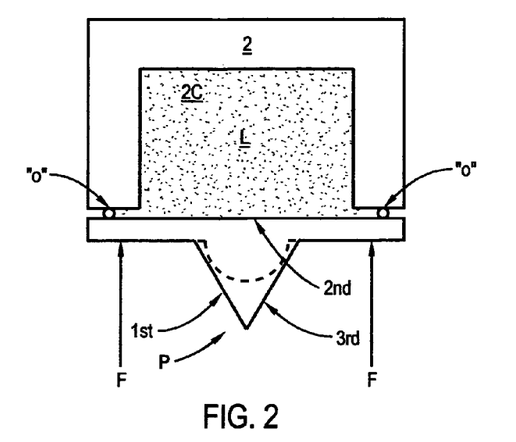
FIGS. 2-4 shows present invention systems for reducing the effects of forces applied to keep system elements in contact with one another, demonstrating both prism (solid lines) and half sphere or half cylinder (dashed lines), shaped elements.

FIG. 2 shows a present invention system for use in investigating optical properties of a liquid comprising:

a prism (P) element comprising first (1st), second (2nd) and third (3rd) substantially flat sides, the second (2nd) side of which is extended laterally beyond projected meeting points with the first 1st and third (3rd) sides;

a second (2) element comprising closed sides and top and an open bottom;

the extended second (2nd) side of said prism (P) being placed into functional contact with said second (2) element at the bottom thereof, typically via at least one gasket or "O" ring or the like means to provide a seal to fluid, to form a liquid (L) containing cavity (2C); such that leakage of liquid which is caused to be present in said liquid containing cavity does not occur through said contact point;

such that in use liquid (L) can be caused to be present in said liquid (L) containing cavity (2C) and electromagnetic radiation can be caused to enter said first (1st) or third (3rd) side of said prism (P), interact with said second (2nd) side thereof, and totally internally reflect through said third (3rd) or first (1st) side thereof, respectively.

Figure 3:
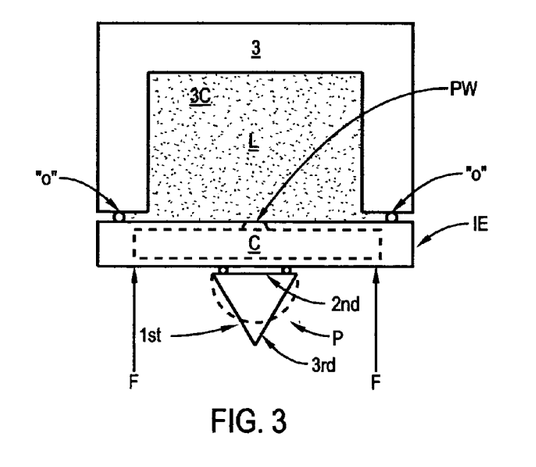

FIG. 3 shows a system for use in investigating optical properties of a liquid comprising:

a prism comprising first (1st), second (2nd) and third (3rd) substantially flat sides;

an intermediate element (IE);

a third (3) element comprising closed sides and top and an open bottom;

wherein said second (2nd) side of said prism (P) is affixed to said intermediate element (IE) by substantially stress free means, and wherein said intermediate element (IE) when placed into functional contact with the bottom of said third (3) element forms a liquid (L) containing cavity (3C), said third (3) element and intermediate element (IE) being forced into contact with one another such that leakage of liquid (L) caused to be present in said liquid containing cavity (3C) does not occur through said contact point;

such that in use liquid can be caused to be present in said liquid containing cavity (3C) and electromagnetic radiation can be caused to enter said first (1st) or third (3rd) side of said prism (P), interact with said second (2nd) side thereof, totally internally reflect and exit through said third (3rd) or first (1st) side thereof.

As shown, said intermediate element (IE) can comprise a cavity (C) sequestered therewithin, and said cavity (C), when present, can be filled with a fluid, such as the liquid (L). Alternatively, such a cavity (C) in the intermediate element (IE) can be continuous with the liquid (L) containing cavity (C) of the third (3) element. Further, it is noted that the interface between the prism (P) and the intermediate element (IE) can have an index of refraction matching liquid present therewithin.

It is noted that the FIG. 2 system results from the FIG. 3 system if a solid, (eg. no cavity (C) present therein), intermediate element (IE) is physically merged with the prism (P). When present, the cavity (C) of the intermediate element (IE) can be continuous with, via a pathway (PW), said liquid containing cavity (3C) of the third element (3), so that the same liquid (L) is present in both.

Figure 4:
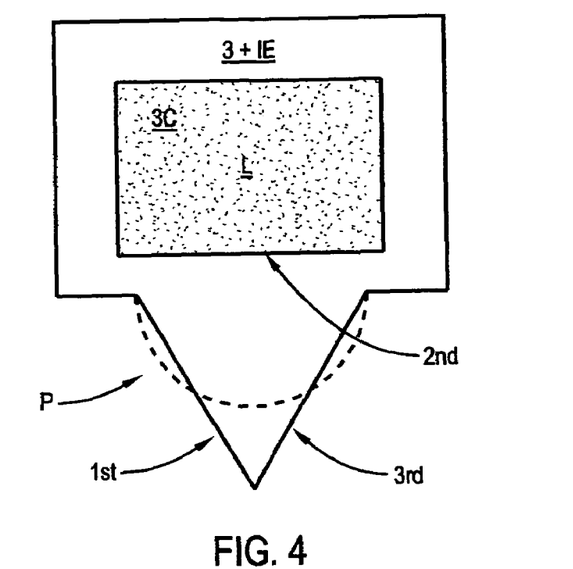

FIG. 4 shows an embodiment which provides that the prism (P) and intermediate element (IE) are merged and of single piece construction. This system results in the prism (P) and second (2) element of FIG. 2 are physically merged.

Figure 5:
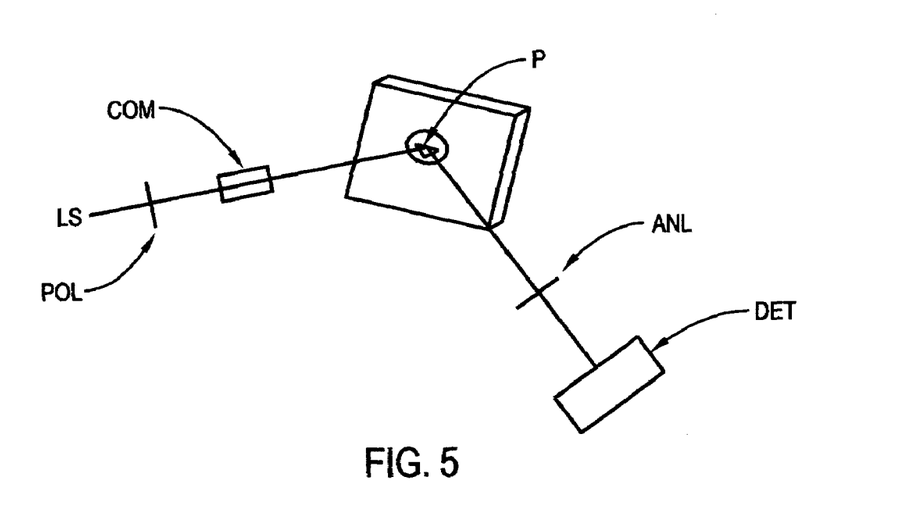
FIG. 5 demonstrates an ellipsometer system.

FIG. 5 shows a general ellipsometer system. A source of electromagnetic radiation (LS) provides a beam of electromagnetic radiation which is caused to pass through a polarizer (POL) enter and exit the prism (P), pass through an analyzer (ANL) and enter a detector (DET). A compensator (COM) is also shown. In use any of the elements (POL), (COM) or (ANL) can be caused to rotate.

Note also that FIGS. 1-4 indicate that, as indicated in dashed lines, the prism can be replaced with a half sphere or half cylinder. The important point being that electromagnetic radiation can enter and exit along a locus which is perpendicular to the surface thereof. The identifier "P" should be interpreted to identify curved or straight intersecting sides.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for use in investigating optical properties of a liquid comprising:

a prism element comprising first, second and third substantially flat sides, the second side of which is extended laterally beyond projected meeting points with the first and third sides;

a second element comprising closed sides and top and an open bottom;

the laterally extended second side of said prism being placed into functional contact with said second element at the bottom thereof to form a liquid containing cavity; such that leakage of liquid, which liquid is caused to be present in said liquid containing cavity, does not occur through said contact point;

such that in use liquid is caused to be present in said liquid containing cavity and electromagnetic radiation is caused to enter said first or third side of said prism, interact with said second side thereof, and totally internally reflect through said third or first side thereof, respectively.

2. A system as in claim 1, which is rotated to orient the open bottom to face other than downward.

3. A system for use in investigating optical properties of a liquid comprising:

a prism comprising first (1st), second (2nd) and third (3rd) substantially flat sides;

an intermediate element (IE);

a third (3) element comprising closed sides and top and an open bottom;

wherein said second (2nd) side of said prism (P) is affixed to said intermediate element (IE) by substantially stress free means, and wherein said intermediate element (IE) when placed into contact with the bottom of said third (3) element forms a liquid (L) containing cavity (3c), said third (3) element and intermediate element (IE) being forced into functional contact with one another such that leakage of liquid (L), which liquid is caused to be present in said liquid containing cavity (3C), does not occur through said contact point;

such that in use liquid can be caused to be present in said liquid containing cavity (3C) and electromagnetic radiation can be caused to enter said first (1st) or third (3rd) side of said prism (P), interact with said second (2nd) side thereof, totally internally reflect and exit through said third (3rd) or first (1st) side thereof.

4. A system and in claim 3 in which said intermediate element comprises a cavity sequestered therewithin.

5. A system as in claim 4, in which said intermediate element cavity is filled with a fluid.

6. A system and in claim 3 in which the cavity of the intermediate element is continuous with the liquid containing cavity of the third element.

7. A system as in claim 3 in which the prism and intermediate element are of single piece construction.

8. A system as in claim 3, which is rotated to orient the open bottom to face other than downward.

9. A system for use in investigating optical properties of a liquid comprising:

a half sphere or half cylinder element comprising a first curved and second substantially flat side, the second side of which is extended laterally beyond the points of intersection of first curved side;

a second element comprising closed sides and top and an open bottom;

the laterally extended second side of said half sphere or half cylinder being placed into functional contact with said second element at the bottom thereof to form a liquid containing cavity; such that leakage of liquid, which liquid is caused to be present in said liquid containing cavity, does not occur through said contact point;

such that in use liquid is caused to be present in said liquid containing cavity and electromagnetic radiation is caused to enter said first curved side of said half sphere or half cylinder, interact with said second side thereof, totally internally reflect therefrom and exit through said first curved side thereof, respectively.

10. A system and in claim 9 in which said intermediate element comprises a cavity sequestered therewithin.

11. A system and in claim 9 in which the cavity of the intermediate element is continuous with the liquid containing cavity of the third element.

12. A system as in claim 9 in which the half sphere or half cylinder and intermediate element are of single piece construction.

13. A system as in claim 9, which is rotated to orient the open bottom to face other than downward.

14. A system for use in investigating optical properties of a liquid comprising:
- a half sphere or half cylinder comprising first (1st) curved and second (2nd) substantially flat side;
- an intermediate element (IE);
- a third (3) element comprising closed sides and top and an open bottom;
- wherein said second (2nd) substantially flat side of said half sphere or half cylinder (P) is affixed to said intermediate element (IE) by substantially stress free means, and wherein said intermediate element (IE) when placed into contact with the bottom of said third (3) element forms a liquid (L) containing cavity (3C), said third (3) element and intermediate element (IE) being forced into functional contact with one another such that leakage of liquid (L), which liquid is caused to be present in said liquid containing cavity (3C), does not occur through said contact point;
- such that in use liquid can be caused to be present in said liquid containing cavity (3C) and electromagnetic radiation can be caused to enter said first (1st) curved side of said half sphere or half cylinder (P), interact with said second (2nd) substantially flat side thereof, totally internally reflect therefrom and exit through said first half sphere or half cylinder first (1st) curved side thereof.

15. A system as in claim 10, in which said intermediate element cavity is filled with a fluid.

16. A system as in claim 14, which is rotated to orient the open bottom to face other than downward.

17. A method of determining the optical properties of a liquid comprising the steps of:
a) providing a system for use in investigating optical properties of a liquid comprising a selection from the group consisting of:
- a prism element comprising first, second and third substantially flat sides, the second side of which is extended laterally beyond projected meeting points with the first and third sides; and
- a half sphere or half cylinder element comprising a first curved and second substantially flat side, the second side of which is extended laterally beyond the points of intersection of first curved side;
- said system further comprising a second element comprising closed sides and top and an open bottom;

the laterally extended second side of said prism, half sphere or half cylinder element being placed into functional contact with said second element at the bottom thereof to form a liquid containing cavity, such that leakage of liquid, which liquid is caused to be present in said liquid containing cavity, does not occur through said contact point;

such that in use liquid can be caused to be present in said liquid containing cavity and electromagnetic radiation can be caused to enter said first curved side of said half sphere or half cylinder element, or enter said first or third side of said prism, interact with said second substantially flat side of said half sphere or half cylinder element or said prism, totally internally reflect therefrom and exit through said first curved side of said half sphere or half cylinder element or said third or first side thereof, respectively;

b) causing said liquid containing cavity to contain a liquid;

c) causing electromagnetic radiation to enter said first curved side of said half sphere or half cylinder element or enter said first or third side of said prism, interact with said substantially flat second side thereof, totally internally reflect and exit through said curved side of said half sphere or half cylinder element or said third or first side thereof respectively and enter a detector;

d) analyzing data provided by the detector in response to the electromagnetic radiation that enters thereinto to the end that optical properties of the liquid are determined.

18. A method as in claim 17, which comprises an additional step comprising rotating the system to orient the open bottom to face other than downward.

* * * * *